United States Patent
Ekin (10) Patent No.: US 11,610,329 B2
(45) Date of Patent: Mar. 21, 2023

(54) VISUALIZATION SYSTEM FOR VISUALIZING AN ALIGNMENT ACCURACY

(71) Applicant: KONINKLIJKE PHILIPS N.V., Eindhoven (NL)

(72) Inventor: Ahmet Ekin, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 63 days.

(21) Appl. No.: 16/981,315

(22) PCT Filed: Mar. 18, 2019

(86) PCT No.: PCT/EP2019/056640
§ 371 (c)(1),
(2) Date: Sep. 16, 2020

(87) PCT Pub. No.: WO2019/179906
PCT Pub. Date: Sep. 26, 2019

(65) Prior Publication Data
US 2021/0012526 A1    Jan. 14, 2021

(30) Foreign Application Priority Data
Mar. 22, 2018    (EP) ..................................... 18163222

(51) Int. Cl.
*G06T 7/73*    (2017.01)
*A61B 34/20*    (2016.01)
*A61B 90/00*    (2016.01)

(52) U.S. Cl.
CPC ................ *G06T 7/73* (2017.01); *A61B 34/20* (2016.02); *A61B 2034/2065* (2016.02);
(Continued)

(58) Field of Classification Search
CPC .............. A61B 90/37; A61B 2090/364; A61B 2090/376; A61B 2034/2065; A61B 34/20;
(Continued)

(56) References Cited

U.S. PATENT DOCUMENTS

| 2007/0249967 | A1* | 10/2007 | Buly ..................... A61B 5/1121 600/595 |
| 2008/0119725 | A1* | 5/2008 | Lloyd ..................... A61B 90/36 600/424 |
| 2014/0114180 | A1 | 4/2014 | Jain |

(Continued)

FOREIGN PATENT DOCUMENTS

| WO | 2015010859 | 1/2015 |
| WO | 2015/062898 | 5/2015 |
| WO | 2016041793 | 3/2016 |

OTHER PUBLICATIONS

International Search Report and Written Opinion dated May 7, 2019 for International Application No. PCT/EP2019/056640 Filed Mar. 18, 2019.

(Continued)

*Primary Examiner* — Pinalben Patel (57) ABSTRACT

The invention relates to a visualization system (10) for visualizing an accuracy of an alignment of a position and shape of an instrument (33), which has been determined by a position and shape determination device (9), with an image of the instrument. The accuracy is determined for different regions of the instrument as defined by the position and shape and of the image, wherein among these regions at least one region is determined, in which the determined accuracy indicates that it is insufficient. A visualization is then generated in which the determined region is indicated on a representation of the position and shape and/or the image. This visualization guides a user's eyes to the region which should not be missed, while deciding whether, for instance, (Continued)

a navigation of the instrument during a subsequent interventional procedure should be based on this alignment, which in turn allows for an improved navigation accuracy.

11 Claims, 7 Drawing Sheets

(52) U.S. Cl.
CPC ............... *A61B 2090/364* (2016.02); *A61B 2090/3764* (2016.02); *G06T 2207/10116* (2013.01); *G06T 2207/20021* (2013.01); *G06T 2207/20081* (2013.01)

(58) Field of Classification Search
CPC ............ A61B 34/25; A61B 2090/3764; A61B 2034/2061; G06T 2207/20021; G06T 7/73; G06T 2207/10116; G06T 2207/30021; G06T 2207/20081
See application file for complete search history.

(56) References Cited

U.S. PATENT DOCUMENTS

| 2016/0171714 A1 | 6/2016 | Ahmet |
| 2016/0253804 A1* | 9/2016 | Ekin ..................... G06T 7/30 382/131 |
| 2017/0119473 A1 | 5/2017 | Clopp |

OTHER PUBLICATIONS

Frangi, et al: "Multiscale vessel enhancement filtering", Medical Image Computing and Computer-Assisted Intervention—MICCAI '98, vol. 1496, pp. 130 to 137 (1998).

* cited by examiner

VISUALIZATION SYSTEM FOR VISUALIZING AN ALIGNMENT ACCURACY

CROSS REFERENCE TO RELATED APPLICATIONS

This application is the U.S. National Phase application under 35 U.S.C. § 371 of International Application No. PCT/EP2019/056640 filed Mar. 18, 2019, which claims the benefit of European Patent Application Number 18163222.5 filed Mar. 22, 2018. These applications are hereby incorporated by reference herein.

FIELD OF THE INVENTION

The invention relates to a visualization system, method and computer program for visualizing an accuracy of an alignment of a position and shape of an instrument with an image of the instrument. The invention relates further to an interventional system for performing an image-guided interventional procedure which comprises the visualization system.

BACKGROUND OF THE INVENTION

Interventional systems for performing an image-guided interventional procedure often comprise an x-ray imaging device for generating x-ray images of a subject and an interventional instrument for being introduced into the subject and for carrying out the interventional procedure. The position and shape of the interventional instrument is determined by using known tracking techniques like optical shape sensing, wherein the determined position and shape of the interventional instrument is registered with the x-ray images generated by the x-ray imaging device, in order to provide a visualization showing the position and shape of the interventional instrument within the subject, i.e. an overlay of a representation of the position and shape of the interventional instrument as determined by using the tracking technique on an x-ray image of the interventional instrument can be shown to a user, in order to allow the user to assess the quality of the registration and to accept or reject the registration. If the user rejects the registration, the registration procedure can be carried out again with another input, i.e., for instance, with other x-ray images, which have been acquired in modified acquisition directions, and/or with other positions and shapes of the interventional instrument.

The evaluation of the registration results requires the user to inspect the alignment between the position and shape of the interventional instrument as determined by the position and shape determination device and the x-ray images. This evaluation adds some mental load on the user, who is often the surgeon, when he/she is generally already pressed for time. This can result in misjudgments regarding the accuracy of the registration such that imperfect registration results may be accepted by the user, wherein this in turn can reduce the navigation accuracy during the image-guided interventional procedure.

SUMMARY OF THE INVENTION

It is an object of the present invention to provide a visualization system, method and computer program for visualizing an accuracy of an alignment of a position and shape of an instrument, which has been determined by a position and shape determination device, with an image of the instrument, which allows for an improved assistance of a user for accepting or rejecting the alignment. It is a further object of the present invention to provide an interventional system for performing an image-guided interventional procedure which comprises the visualization system.

In a first aspect of the present invention a visualization system for visualizing an accuracy of an alignment of a position and shape of an instrument, which has been determined by a position and shape determination device, with an image of the instrument is presented, wherein the visualization system comprises:

a position, shape and image providing unit configured to provide a) the position and shape and b) the image which are aligned to each other, an accuracy determination unit configured to determine the accuracy of the alignment based on the position and shape and based on the image, wherein the accuracy determination unit is configured to determine the accuracy for different regions of the instrument as defined by the position and shape and of the image and to determine a region, in which the determined accuracy indicates that it is insufficient, and a visualization unit configured to generate a visualization of the accuracy, wherein the visualization unit is configured to generate the visualization such that the determined region is indicated on at least one of a) a representation of the position and shape and b) the image.

Since the accuracy determination unit is able to determine the accuracy for different regions of the image and hence of the instrument as defined by the position and shape, which has been determined by the position and shape determination device, since among these regions the region is determined, in which the accuracy is insufficient, and since the visualization unit then generates a visualization of the accuracy by indicating the determined region on at least one of the image and a representation of the position and shape of the instrument, the user's eyes are guided to the region of the representation of the position and shape and/or of the image, which should be reviewed, i.e. which should not be missed, while deciding whether the alignment should be accepted or rejected. This improves the quality of the acceptance or rejection procedure, even if the user is under time pressure, which in turn leads to an improved navigation accuracy during a subsequent interventional procedure.

Since the position and shape of the instrument and the image are aligned to each other, each region of the instrument as defined by the position and shape is aligned with a corresponding region of the image such that by determining the accuracy for a region of the instrument as defined by the position and shape also the accuracy for the corresponding image region is determined and vice versa.

The position, shape and image providing unit can be a storing unit in which the position and shape and the image, which are aligned to each other, are stored and from which the position and shape and the image can be retrieved for providing the same. The position, shape and image providing unit can also be a receiving unit for receiving the position and shape and the image from another device, i.e., for instance, from an imaging device and a position and shape determination device directly or via a registration device which has already registered the position and shape and the image to each other, and for providing the received position and shape and image. The position, shape and image providing unit can also be a registration device for registering a position and shape of an instrument and an image of the instrument and for providing the registered position and shape and image.

Preferentially, the visualization unit is configured to generate the visualization such that the representation of the position and shape of the instrument is overlaid on the image, wherein a part of the representation of the position and shape, which corresponds to the determined region, and/or the corresponding region of the image are highlighted, in order to indicate the determined region.

In an embodiment the accuracy determination unit is configured to a) determine a projection of the instrument as defined by the provided position and shape onto the image under consideration of an image acquisition geometry which had been used for generating the provided image, b) determine distances for parts of the projection, wherein, for determining a distance for a part of the projection, the distance to a nearest location in the image is determined, at which a part of the instrument is detectable in the image by using a predefined instrument detection algorithm, and c) determine the accuracy based on the determined distances. Moreover, in an embodiment the accuracy determination unit is configured to subdivide the instrument as defined by the provided position and shape into regions and to determine the accuracy for each region of the instrument separately, in order to determine for different regions of the instrument as defined by the provided position and shape and of the image respective accuracies. Determining the spatial accuracies in this way leads to a very reliable assistance of the user while reviewing the position and shape and the image which are aligned to each other.

Preferentially, the accuracy determination unit is configured to, for determining a distance for a part of the projection, determine the distance only within an area around the part having a predefined size. This can lead to a reduction of the computational efforts, wherein the predefined size can be chosen such that still a reliable assistance can be provided to the user. The predefined size can be determined by calibration, wherein data sets of positions and shapes of an instrument and images of the instrument and of known accuracies can be used, wherein during the calibration procedure the predefined size can be determined such that, given the data set of positions and shapes and images, a reliable assistance is provided to the user. The predefined size of the area around the respective part of the projection on the image can be given as a physical size or as a number of image elements like pixels which should be considered around the respective part of the projection while determining the distances. If the predefined size is given as physical size like 10 mm, the accuracy determination unit can be configured to transfer this physical size into a corresponding number of image elements which can then be used while determining the distances.

The accuracy determination unit is preferentially configured such that the predefined size depends on the size of the image. Moreover, the accuracy determination unit is preferentially configured such that the predefined size increases with increasing size of the image. In particular, the predefined size increases proportionally with increasing image size. This can lead to a reliable assistance for the user, wherein the reliability of the assistance can be independent of the size of the respective image.

The accuracy determination unit is preferentially configured to determine distance features based on the determined distances and determine the accuracy based on the determined distance features. In particular, the accuracy determination unit is configured to determine the distance features such that they include at least one of a) an average of the determined distances and b) a fraction of the distances being larger than a predefined fraction threshold. It has been found that using these distance features for determining the accuracy leads to a further increased reliability of the assistance of the user.

It is also preferred that the position, shape and image providing unit is configured to provide a further image which shows the instrument and which is aligned with the position and shape, wherein the accuracy determination unit is configured to a) determine a further projection of the instrument as defined by the provided position and shape onto the further image under consideration of a further image acquisition geometry which had been used for generating the provided further image, b) determine further distances for parts of the further projection, wherein, for determining a further distance for a part of the further projection, the distance to a nearest location in the further image is determined, at which a part of the instrument is detectable in the further image by using the predefined instrument detection algorithm, and c) determine the accuracy also based on the determined further distances. In particular, the accuracy determination unit is configured to determine the distance features such that they include at least one of a) a maximum of i) an average of the determined distances and ii) an average of the determined further distances and b) a maximum of i) a fraction of the distances being larger than the predefined fraction threshold and ii) a fraction of the further distances being larger than the predefined fraction threshold. By considering the further image and the further distances while determining the accuracy, the quality of determining the accuracy can be further improved, which can lead to a further increased reliability of the assistance of the user in deciding whether to accept or reject the alignment.

The accuracy determination unit can be adapted to determine a binary accuracy, i.e. the accuracy determination unit can be adapted to determine for different regions whether for the respective region the accuracy is sufficient or insufficient. It is also possible that there are different classes, which could also be named levels, of accuracy, wherein the accuracy determination unit is adapted to determine for different regions a respective accuracy class and wherein the visualization unit is adapted to indicate at least some of the different accuracy classes by using different visual properties like different colors, different intensities, different symbols, et cetera.

Preferentially, the accuracy determination unit is configured to use a trained classifier for determining the accuracy based on the distance features. Thus, based on a given data set, which includes different positions and shapes and images or already different distance features and which also includes different accuracy classes already determined for these data, a classifier can be trained, wherein then the trained classifier can be used for determining the accuracies for the different regions. In an embodiment the trained classifier uses thresholds, wherein the determined distance features are compared with these thresholds for determining the respective accuracy class.

In an embodiment the position, shape and image providing unit is configured to register the position and shape with the image for providing the alignment between the position and shape and the image.

In a further aspect of the present invention an interventional system for performing an image-guided interventional procedure is presented, wherein the interventional system comprises:

an interventional instrument to be used within a subject,
an imaging device constructed to image the interventional instrument within the subject, a position and shape determination device constructed to determine a position and shape of the interventional instrument within the subject, a visualization system for visualizing an accuracy of an alignment of the position and shape of the interventional instrument with the image of the interventional instrument as defined in claim 1.

In another aspect of the present invention a visualization method for visualizing an accuracy of an alignment of a position and shape of an instrument, which has been determined by a position and shape determination device, with an image of the instrument is presented, wherein the visualization method comprises:

providing a) the position and shape and b) the image which are aligned to each other by a position, shape and image providing unit, determining the accuracy of the alignment based on the position and shape and based on the image by an accuracy determination unit, wherein the accuracy determination unit determines the accuracy for different regions of the instrument as defined by the position and shape and of the image and determines a region in which the determined accuracy indicates that it is insufficient, and generating a visualization of the accuracy by a visualization unit, wherein the visualization unit generates the visualization such that the determined region is indicated on at least one of a) a representation of the position and shape and b) the image.

In an aspect of the present invention a visualization computer program for visualizing an accuracy of an alignment of a position and shape of an instrument, which has been determined by a position and shape determination device, with an image of the instrument, is presented, wherein the computer program comprises program code means for causing a visualization system to carry out the steps of a visualization method, when the computer program is run on a computer controlling the visualization system device.

It shall be understood that the visualization system, the interventional system, the visualization method, and the visualization computer program, have similar and/or identical preferred embodiments, in particular, as defined herein.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

Figure 1:
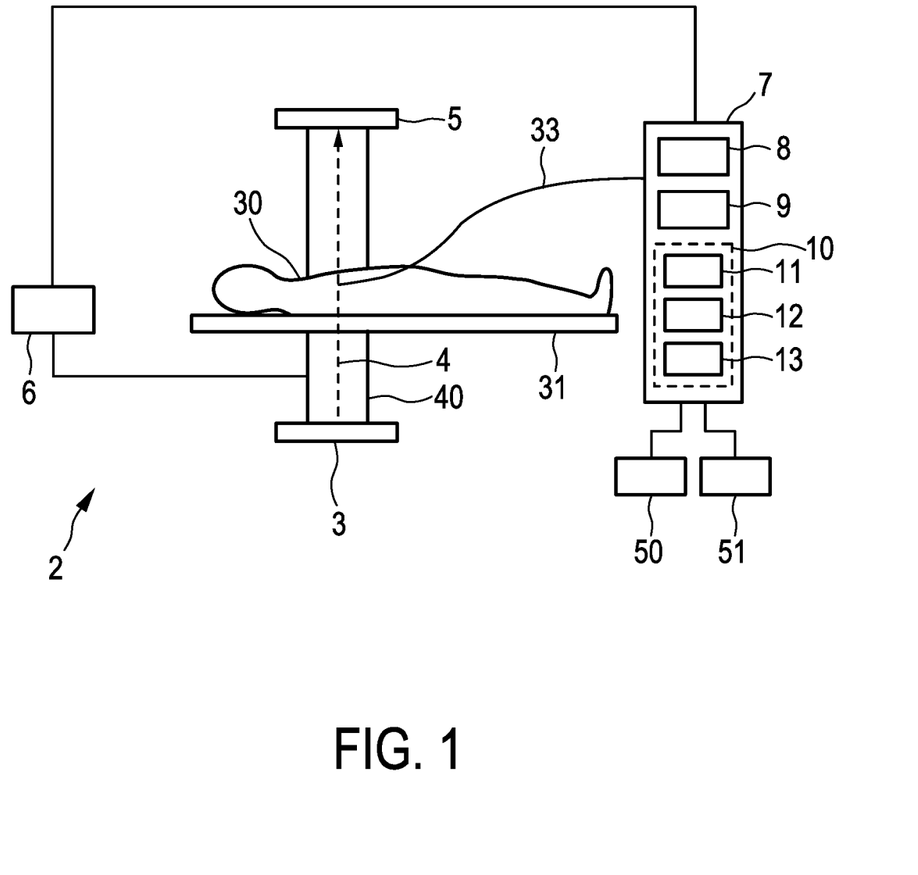
FIG. 1 shows schematically and exemplarily an embodiment of an interventional system for performing an image-guided interventional procedure.

FIG. 1 shows schematically and exemplarily an embodiment of an interventional system for performing an image-guided interventional procedure. In this embodiment the interventional system comprises an interventional instrument 33 to be used within a subject 30, i.e. within a patient, lying on a support means 31 like a support table, wherein in this embodiment the interventional instrument 33 is a guidewire. In another embodiment the interventional instrument 33 can also be another device like a catheter.

The interventional system 1 further comprises an imaging device 2 with a radiation source 3 for emitting x-rays 4 traversing the subject 30 and a detector 5 for detecting the x-rays 4 after having traversed the subject 30. The radiation source 3 and the detector 5 are mounted on a C-arm 40, wherein the imaging device 2 is adapted such that the C-arm 40 with the radiation source 3 and the detector 5 is rotatable relative to the support means 31. This ensures that x-ray images of the subject 30, which also show the interventional instrument 33, can be acquired in different acquisition directions. The C-arm 40, the radiation source 3 and the detector 5 are controlled by a control unit 6 which is also adapted to generate the x-ray images based on detection values received from the detector 5. The acquired x-ray images are transferred to a control and processing unit 7.

The interventional system 1 further comprises a position and shape control unit 8 for controlling the position and shape of the interventional instrument 33. In this embodiment a user can provide an input indicating a desired position and shape of the interventional instrument 33 via an input unit 50, whereafter the position and shape control unit 8 controls the interventional instrument 33 accordingly such that it has the desired position and shape. It should be noted that the setting of the position includes a setting of the location and orientation of the interventional instrument 33 such that by setting the position and shape of the interventional instrument 33 the entire spatial situation with respect to the interventional instrument 33 can be defined. The input unit 33 can be a keyboard, a touch pad, a joystick, et cetera.

In another embodiment the position and shape of the interventional instrument 33 can also be set in another way. For instance, it can be simply directly set by the user manually, whereafter this set position and shape might be fixed by using corresponding fixation means.

The interventional system 1 further comprises a position and shape determination device 9 constructed to determine the position and shape of the interventional instrument 33 by optical shape sensing and a registration device 11 constructed to register the determined position and shape with an image generated by the imaging device 2, which shows the interventional instrument 33.

The registration device 11 is adapted to detect the interventional instrument 33 in an image generated by the imaging device 2 and to use this instrument detection in the image together with the current position and shape of the interventional instrument 33 as provided by the position and shape determination device 9 for registering the image with the determined position and shape and hence for registering the imaging device 2 with the position and shape determination device 9. The detection of the interventional instrument 33 in the image can be carried out fully automatically, semi-automatically or fully manually, wherein for a semi-automatical or manual detection of the interventional instrument 33 in the image the registration device 11 can be adapted to provide a graphical user interface via the input unit 50 and a display 51.

Figure 2:
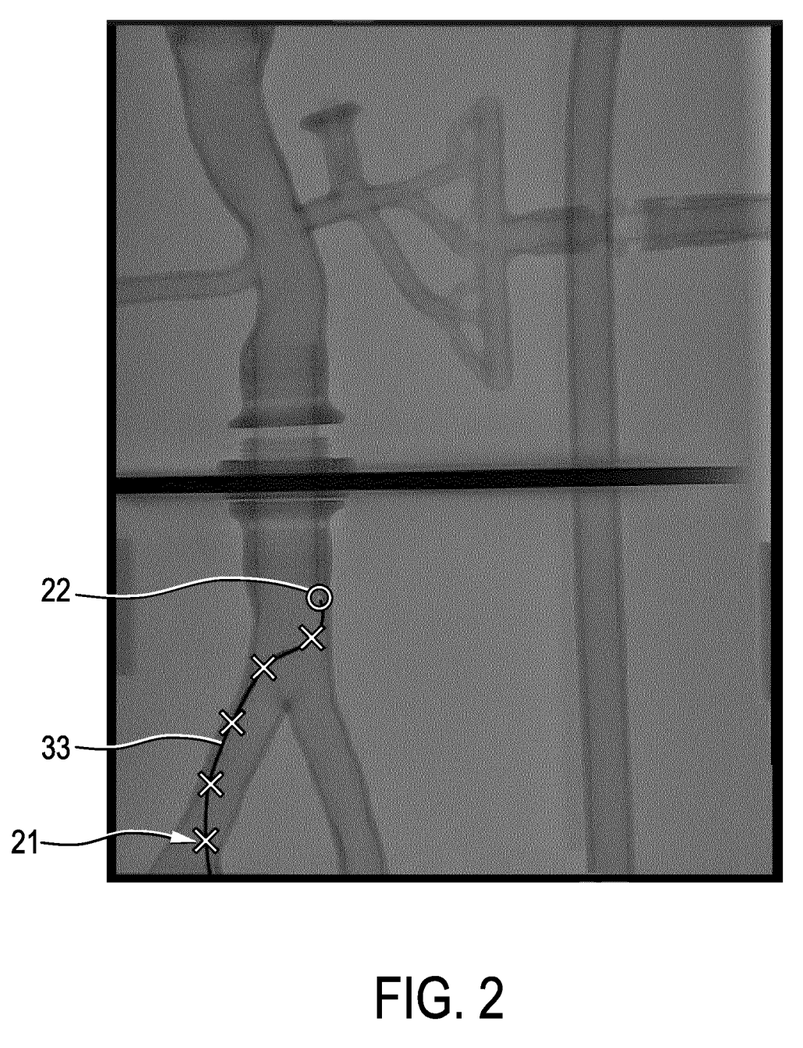
FIG. 2 shows schematically and exemplarily a first image of an interventional instrument with a user-indicated location of the tip of the interventional instrument in the first image and with locations of further parts of the interventional instrument in the first image, which have been automatically determined, wherein the first image has been acquired in a first acquisition direction.
Figure 3:
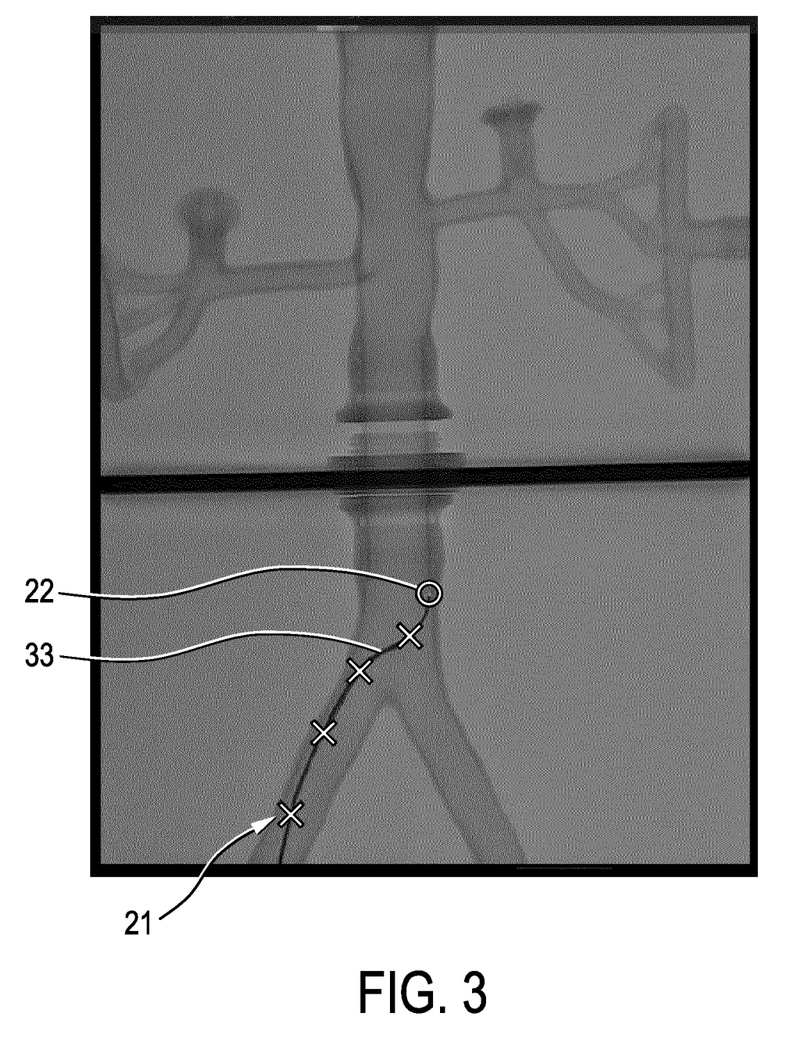
FIG. 3 shows schematically and exemplarily a second image of an interventional instrument with a user-indicated location of the tip of the interventional instrument and with further indications of locations of further parts of the interventional instrument in the second image, which have been determined automatically, wherein the second image has been acquired in a second acquisition direction.

FIGS. 2 and 3 schematically and exemplarily illustrate a graphical user interface which might be provided by the registration device 11 via the display 51. The graphical user interface is adapted such that the user can indicate the position of the tip of the interventional instrument 33 in two images which have been acquired in different acquisition directions by using the imaging device 2. One of these images is shown in FIG. 2 and the other of these two images is shown in FIG. 3. The circle 22 marks the position within these two images indicated by the user as showing the tip of the interventional instrument 33. In this example the registration device 11 is adapted to determine further locations of the interventional instrument 33 in these two images based on the location of the tip of the interventional instrument 33 as indicated by the user and based on an automatic detection of the interventional instrument 33 in these two images. In FIGS. 2 and 3 these further locations are indicated by crosses 21. In particular, the registration device 11 can be adapted to use known segmentation algorithms for determining further locations of the interventional instrument 33 in these two images, wherein the segmentation algorithm can consider that the segmented interventional instrument must include the user-indicated location. In an embodiment the registration device 11 is adapted to use the technique as disclosed in US 2017/358091 A1 for determining the further locations of the interventional instrument 33 in the two images. In another embodiment another known technique can be used for determining locations of an interventional instrument in an image.

Figure 4:
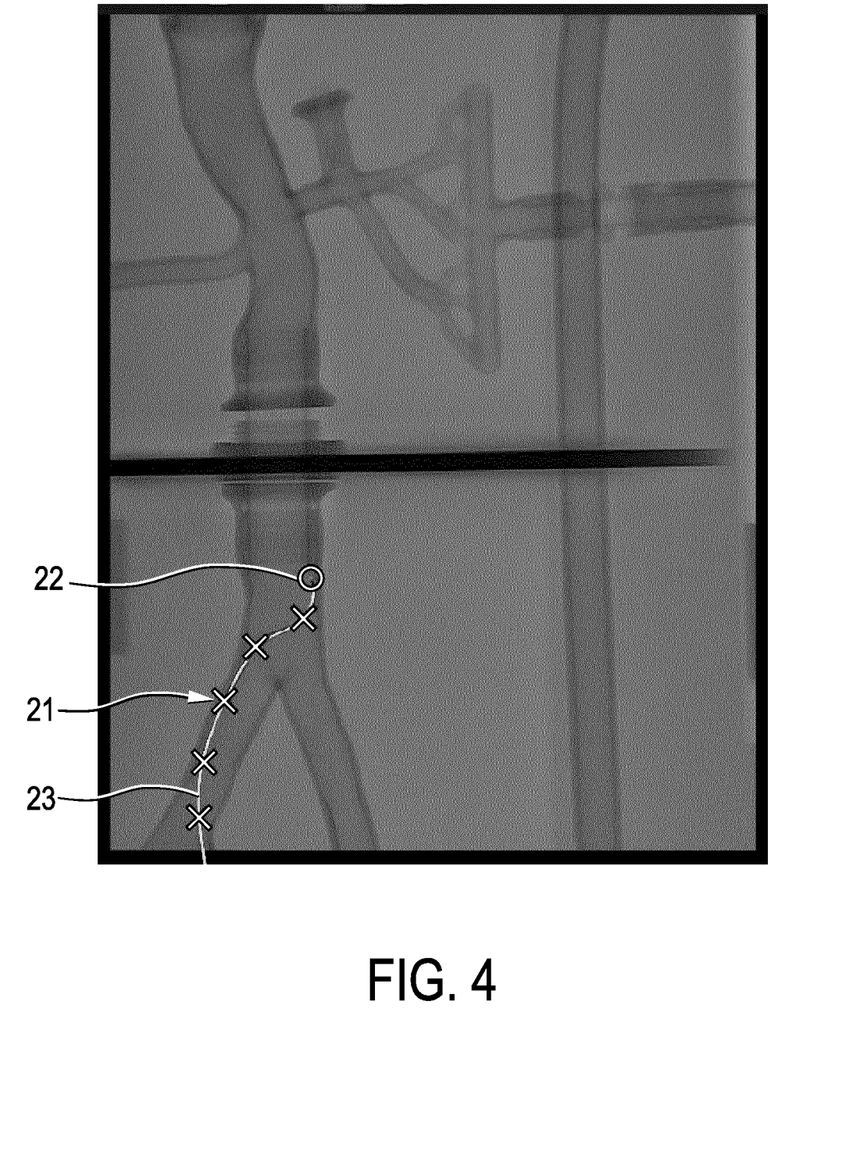
FIG. 4 shows schematically and exemplarily the first image with an additional representation of a position and shape of the interventional instrument as determined by a position and shape determination device.
Figure 5:
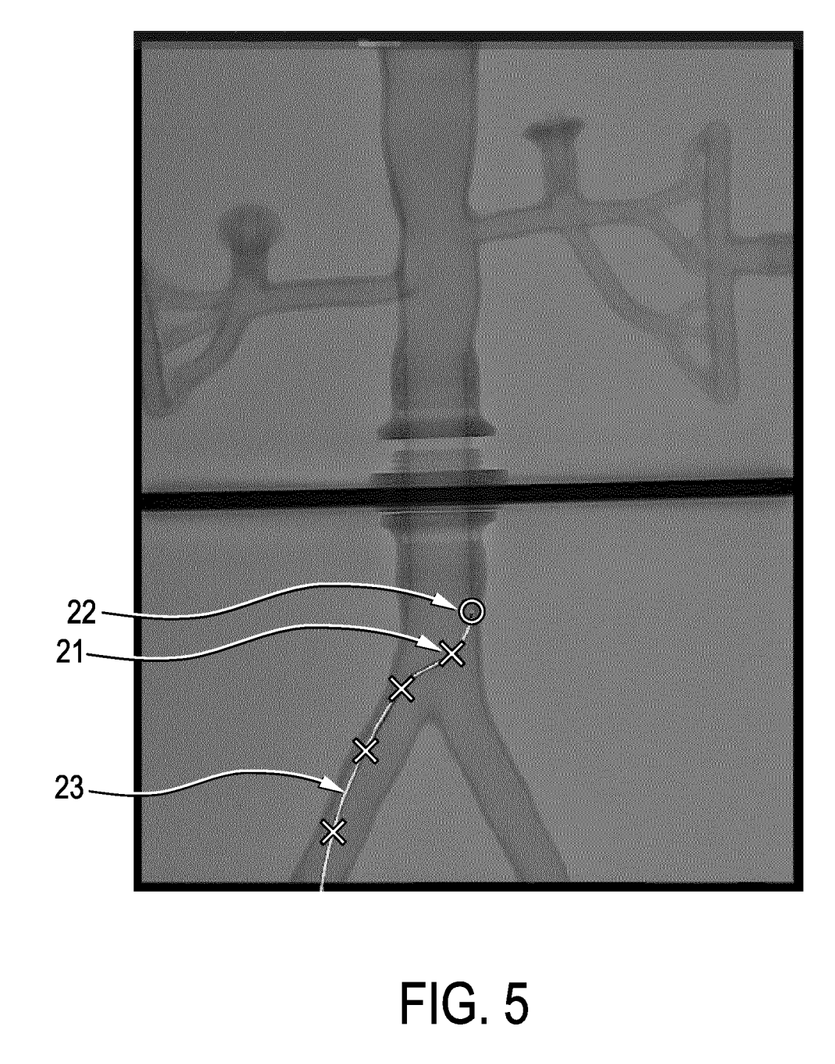
FIG. 5 shows schematically and exemplarily the second image with the additional representation of the position and shape of the interventional instrument as determined by the position and shape determination device.

The registration device 11 is adapted to register the images shown in FIGS. 2 and 3 with the position and shape of the interventional instrument 33 determined by the position and shape determination unit 9 based on the crosses 21 and the user-indicated tip locations 22 and based on the position and shape of the interventional instrument 33 determined by the position and shape determination device 9. The corresponding registration result is illustrated in FIGS. 4 and 5, wherein in these figures only a representation 23 of the position and shape of the interventional instrument 33 can be seen and not the interventional instrument 33 in the image itself, because the position and shape determined by the position and shape determination device 9 is very well aligned with the two images shown in FIGS. 4 and 5. Thus, if the user reviews the registration result as shown in FIGS. 4 and 5, the user will very likely accept the registration such that this registration will be used during a subsequent interventional procedure.

The registration device 11 is preferentially adapted to register the images with the position and shape of the interventional instrument 33 determined by the position and shape determination unit 9 such that deviations between the locations 20, 21 in the images and a projection of the position and shape of the interventional instrument 33 determined by the position and shape determination unit 9 onto the images are minimized, wherein the projections of the position and shape of the interventional instrument as determined by the position and shape determination unit 9 onto the images are simulated under consideration of the respective image acquisition geometry used for generating the images. In an embodiment the registration device 11 is adapted to use the registration method disclosed in US 2016/171714 A1 which is herewith incorporated by reference. In another embodiment also other known registration techniques can be used.

Figure 6:
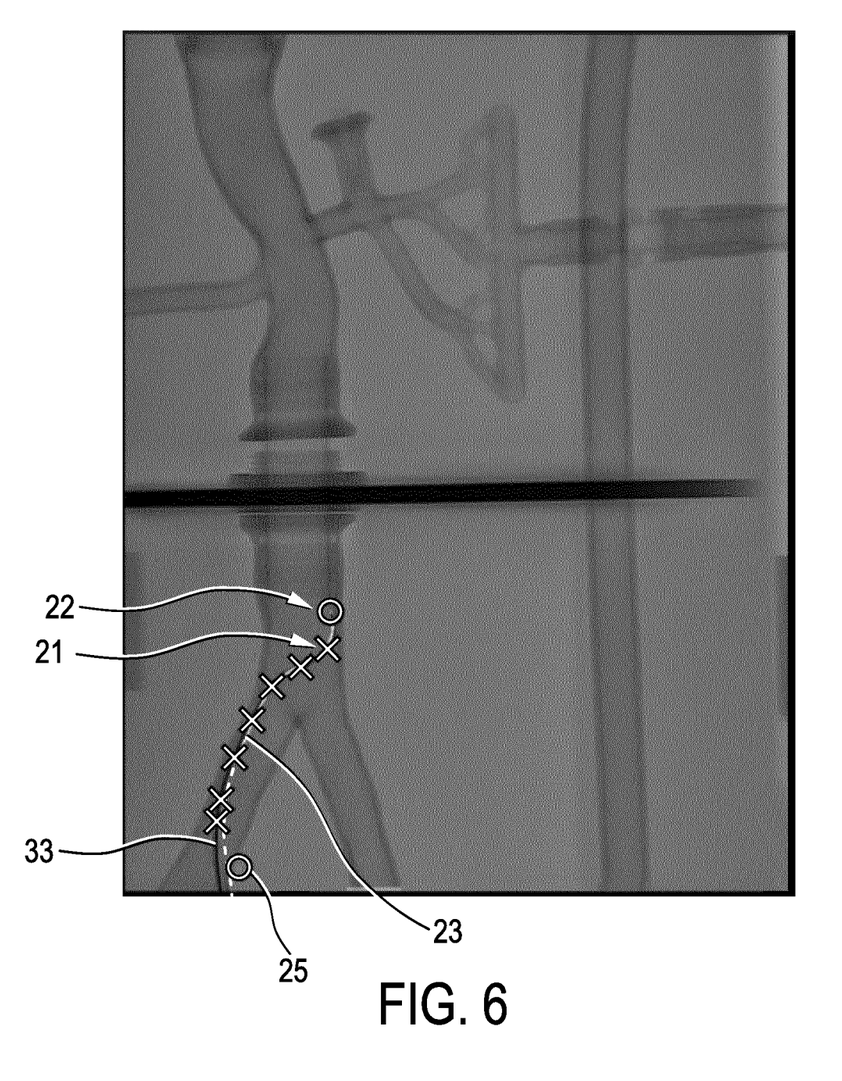
FIG. 6 shows schematically and exemplarily an image of the interventional instrument and a representation of the position and shape of the interventional instrument as determined by the position and shape determination device with a highlighted region of the representation, which indicates an inaccurate alignment between the interventional instrument visible in the image and the position and shape of the interventional instrument as determined by the position and shape determination device.

The interventional system 1 further comprises an accuracy determination unit 12 configured to determine the accuracy of the alignment based on the position and shape and based on at least one of the images, wherein the accuracy determination unit 12 is configured to determine the accuracy for different regions of the interventional instrument 33 as defined by the position and shape and hence of the respective image and to determine a region in which the determined accuracy indicates that it is insufficient. The interventional system further comprises a visualization unit 13 configured to generate a visualization of the accuracy, wherein the visualization unit 13 is configured to generate the visualization such that the determined region is indicated on a representation of the position and shape. This generated visualization can then be output on the display 51. FIG. 6 schematically and exemplarily illustrates such a visualization, wherein in this figure the lower part of the representation 23 of the position and shape of the interventional instrument 33 is highlighted by using another visual property like another color. Since FIG. 6 is a gray scale figure, in this figure the "color" is indicated by the lower broken segment of the representation 23. Also the corresponding region of the image could be highlighted. Besides the instrument positions 21, 22 FIG. 6 shows a further instrument position 25 which has also been indicated by the user, wherein in this example this user-indicated instrument position 25 has led to a bad alignment. It is also possible to highlight the instrument position 25 which led to the bad alignment.

The accuracy determination unit 12 can be configured to determine the instrument position 21, 22, 25 having a largest distance to a projection of the registered position and shape as determined by the position and shape determination device 9, i.e. having a largest distance to the representation 23. In this way in this example the instrument position 25 can be determined and highlighted as being the instrument position which likely led to the bad alignment. The accuracy determination unit 12 can also be adapted to calculate for each of the instrument positions 21, 22, 25 a respective closest distance to the instrument as detected in the respective image, wherein the instrument can be detected in the respective image by using, for instance, known segmentation algorithms. Also a segmentation result, which might have already been used for the registration procedure, can be used for calculating these distances. The instrument position 21, 22, 25, for which the largest distance has been calculated, and/or the instrument position 21, 22, 25, for which a distance being larger than a predefined distance threshold has been determined, can be determined as an instrument position which likely led to the bad alignment.

The accuracy determination unit 12 is configured to determine a projection of the instrument 33 as defined by the provided position and shape onto the respective image under consideration of the respective image acquisition geometry which had been used for generating the provided respective image and to determine distances for parts of the respective projection, wherein, for determining a distance for a part of the respective projection, the distance to a nearest location in the image is determined, at which a part of the instrument is detectable in the respective image by using a predefined instrument detection algorithm. The accuracy determination unit 12 is further configured to determine the accuracy based on the determined distances.

For detecting the instrument 33 in the respective image the accuracy determination unit 12 can use any known instrument detection algorithm, i.e. any instrument segmentation algorithm. It is also possible that the accuracy determination unit 12 does not detect the instrument in the respective image, but uses a corresponding segmentation result which might have been obtained during the registration procedure carried out by the registration device 11. In an embodiment for detecting the instrument in the respective image a vesselness filter can be applied to the respective image like the vesselness filter disclosed in the article "Multiscale vessel enhancement filtering" by A. Franhi et al., Medical Image Computing and Computer-Assisted Intervention—MICCAI '98, volume 1496, pages 130 to 137 (1998) which is herewith incorporated by reference. After the vesselness filter has been applied to the respective image, for each image element a respective vesselness value has been determined which might be normalized. All vesselness values being larger than a predefined vesselness threshold are regarded as indicating locations of parts of the instrument 33 in the respective image, thereby detecting the instrument in the respective image.

The accuracy determination unit 12 is configured to, for determining a distance for a part of the projection, determine the distance only within an area around the part having a predefined size, wherein this predefined size preferentially depends on the size of the image. Each respective image is a two-dimensional image and the image elements are pixels, wherein, for instance, for each pixel of a projection, i.e. for each part of the respective projection, a search can be carried out within an area of n pixels to the left, to the right, above and below, in order to find the nearest instrument-like pixel, i.e. the nearest part of the instrument detectable in the image by using the predefined instrument detection algorithm. In an embodiment the value n is set to 9 for an image with a width of 1024 pixels. This number n, i.e. the search range, increases proportionally with the image width. By determining the distances only within an area around the part of the projection, i.e., for instance, by determining for each image element representing a projection of the provided position and shape distances only within the area having the predefined size, the computational efforts for calculating the distances can be reduced. However, it is also possible to use a segmentation of the instrument resulting from applying a corresponding segmentation algorithm to the complete respective image for determining the distances.

The accuracy determination unit 12 can be configured to use directly the distances for indicating the accuracy. For instance, the image elements of the respective projection, i.e. the parts of the respective projection, for which largest distances and/or distances being larger than a predefined distance threshold have been determined, can be regarded as being likely inaccurate and the corresponding part of the representation and/or the corresponding region of the respective image can be highlighted on the visualization. The accuracy determination unit 12 can also be adapted to determine that image elements of the respective projection are inaccurately aligned, only if for a group of neighboring image elements of the respective projection distances have been determined which are all larger than a predefined distance threshold, wherein only then the respective part of the representation is highlighted on the visualization as being inaccurate.

In an embodiment the accuracy determination unit 12 is configured to determine distance features based on the determined distances and to determine the accuracy based on the determined distance features. In particular, the accuracy determination unit 12 is configured to determine an average of the distances determined for a first image which has been acquired in a first acquisition direction and a fraction of the distances being larger than a predefined fraction threshold for the first image. The accuracy determination unit 12 is further configured to determine these values also for a second image which has been acquired in a second acquisition direction. The predefined fraction threshold can be determined by calibration, particularly by training a classifier, wherein in an embodiment this predefined fraction threshold is 2.5.

Moreover, the accuracy determination unit 12 can be configured to determine following distance features for determining the accuracy: a) the maximum of i) the average of the distances determined for the first image and ii) the average of the distances determined for the second image, and b) the maximum of i) the fraction of the distances, which have been determined for the first image and which is larger than the predefined fraction threshold, and ii) the fraction of the distances which have been determined for the second image and which are larger than the predefined fraction threshold. For providing a further distance feature a similarity measure, which has been employed by the registration procedure, can be used, wherein this similarity measure increases with decreasing deviations between the position and shape of the interventional instrument as shown in the image and the position and shape of the interventional instrument as defined by the position and shape determined by the position and shape determination device 9. The result of this similarity measure can be regarded as being a further distance feature. Thus, in an embodiment for determining the accuracy a maximum average distance feature, a maximum fraction distance feature and a similarity distance feature can be used.

A classifier can be trained by using a training set including many maximum average distance features, maximum fraction distance features and similarity distance features for many different images and many different positions and shapes of an instrument and with assignments whether the respective alignment was regarded as being accurate enough or not. With such a training set the classifier can be trained such that the accuracy determination unit provides a binary accuracy, i.e. whether the alignment is sufficiently accurate or not. The classifier can also be trained with training sets comprising more than two different accuracy classes, in order to allow the accuracy determination unit 12 by using the trained classifier to provide different levels of accuracy. For instance, the classifier can be trained such that three classes of accuracy are present, wherein the visualization unit 13 can be adapted to indicate these three different classes by using three different visual properties like three different colors, for instance, green, yellow and red. These visual properties can be used for highlighting the different parts of the image and/or of the representation of the position and shape as defined by the position and shape determined by the position and shape determination device 9 differently depending on the accuracy determined for the different parts. For instance, if the representation of the position and shape as determined by the position and shape determination device 9 is entirely green, the alignment is accurate for the entire interventional instrument visible in the images, whereas, if, for example, for a certain part of the position and shape the alignment is inaccurate, the corresponding part of the representation can be highlighted in red.

In an embodiment the training of the classifier leads to a similarity distance threshold of 1.75, a maximum average distance threshold of 0.3 and a maximum fraction threshold of 0.16. Thus, in an embodiment it is determined that the determined accuracy indicates a sufficient accuracy, if the similarity distance feature is larger than 1.75, the maximum average distance feature is larger than 0.3 and the maximum fraction distance feature is larger than 0.16. In other embodiments these thresholds can have other values. This classifier, which is based on three thresholds, requires relatively low computational efforts, is hence very fast and nevertheless allows for a very accurate calculation of the accuracy. However, in another embodiment also another classifier can be used like a Random Forest classifier or a Naïve Bayes classifier.

The accuracy determination unit 12 can be configured to subdivide the instrument 33 as defined by the provided position and shape, i.e. to subdivide in fact the provided shape, into regions, which might also be named segments, and to determine the accuracy for each region or segment of the instrument separately, in order to determine for different regions or segments of the instrument as defined by the provided position and shape and correspondingly for the regions of the image respective accuracies. For instance, for each region or segment of the instrument as defined by the provided position and shape distance features can be calculated and the classifier can be used for determining based on the respective distance features an accuracy class for the respective region or segment of the instrument as defined by the provided position and shape, wherein these accuracy classes determined for the different regions or segments of the instrument as defined by the provided position and shape can be visualized on the representation of the provided position and shape of the instrument and/or in corresponding regions of the respective image.

Figure 7:
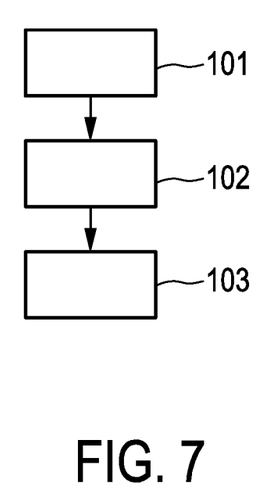
FIG. 7 shows a flowchart exemplarily illustrating an embodiment of a visualization method for visualizing an accuracy of an alignment of a position and shape of an instrument, which has been determined by a position and shape determination device, with an image of the instrument.

In the following an embodiment of a visualization method will exemplarily be described with reference to a flowchart shown in FIG. 7.

In step 101 the current position and shape of the interventional instrument 33 as determined by the position and shape determination device 9 and first and second images are provided by the position, shape and image providing unit 11, wherein the first image and the second image have been acquired in different acquisition directions and show the interventional instrument 33 in its current position and shape. In this embodiment the position, shape and image providing unit 11 is a registration device which has already registered the position and shape as determined by the position and shape determination device 9 with the first and second images provided by the imaging device 2.

In step 102 the accuracy of the alignment between a) the position and shape determined by the position and shape determination device 9 and b) the first and second images showing the interventional instrument in its current position and shape is determined by the accuracy determination unit 12, wherein the accuracy determination unit 12 determines the accuracy for different regions of the interventional instrument 33 as defined by the position and shape determined by the position and shape determination device 9 and correspondingly for different regions of the images showing the interventional instrument and it determines a region in which the determined accuracy indicates that it is insufficient. For instance, for different regions the accuracies can be determined by using a trained classifier which determines for each region an accuracy value or accuracy class indicating a sufficient accuracy or an accuracy value or accuracy class indicating an insufficient accuracy.

In step 103 a visualization of the accuracy is generated by the visualization unit 13, wherein the visualization unit 13 generates the visualization such that one or several regions for which an insufficient accuracy has been determined are highlighted on at least one of a) a representation of the position and shape as determined by the position and shape determination device 9 and b) the first and second images.

The position, shape and image providing unit 11 being, in the embodiment described above with reference to FIG. 1, a registration device, the accuracy determination unit 12 and the visualization unit 13 can be regarded as forming a visualization system 10 for visualizing the accuracy of the alignment of the position and shape of the interventional instrument, which has been determined by the position and shape determination device 9, with the images of the interventional instrument.

If it is visualized that at least for an imaged part of the interventional instrument the alignment is inaccurate, the user will not miss this part when deciding whether to accept or reject the current alignment. If the user rejects the current alignment, the user can modify, for instance, the acquisition directions for acquiring the images and/or the current position and shape of the interventional instrument, whereafter the registration device 11 can register the position and shape as determined by the position and shape determination device and the images again. The accuracy determination unit 12 can then also again determine the accuracies which can then be used for updating the visualization. Thus, the user can modify, for instance, the position and shape of the interventional instrument and/or the acquisition directions for acquiring the images until the generated visualization indicates that there is no inaccurate region any more.

Although in above described embodiments the interventional instrument is a guidewire, the interventional instrument can also be another device which is configured to allow for a determination of its position and shape by, for instance, optical shape sensing like a correspondingly enabled catheter, needle, sheath et cetera.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Procedures like the determination of the accuracy, the generation of the visualization, et cetera performed by one or several units or devices can be performed by any other number of units or devices. These procedures and/or the control of the visualization system in accordance with the visualization method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a visualization system for visualizing an accuracy of an alignment of a position and shape of an instrument, which has been determined by a position and shape determination device, with an image of the instrument. The accuracy is determined for different regions of the instrument as defined by the position and shape and of the image, wherein among these regions at least one region is determined, in which the determined accuracy indicates that it is insufficient. A visualization is then generated in which the determined region is indicated on a representation of the position and shape and/or the image. This visualization guides a user's eyes to the region which should not be missed, while deciding whether, for instance, a navigation of the instrument during a subsequent interventional procedure should be based on this alignment, which in turn allows for an improved navigation accuracy.

The invention claimed is:

1. A visualization system for visualizing an accuracy of an alignment of a position and shape of an instrument, which has been determined by a position and shape determination device, with an image of the instrument, wherein the visualization system comprises:
   a position, shape and image providing unit configured to provide a) the position and shape and b) the image which are aligned to each other,
   an accuracy determination unit configured to determine the accuracy of the alignment based on the position and shape and based on the image, wherein the accuracy determination unit is configured to determine the accuracy for different regions of the instrument as defined by the position and shape and of the image and to determine a region, in which the determined accuracy indicates that it is insufficient, and
   a visualization unit configured to generate a visualization of the accuracy, wherein the visualization unit is configured to generate the visualization such that the determined region is indicated on at least one of a) a representation of the position and shape and b) the image;
   wherein the accuracy determination unit is configured to a) determine a projection of the instrument as defined by the provided position and shape onto the image under consideration of an image acquisition geometry which had been used for generating the provided image, b) determine distances for parts of the projection, wherein, for determining a distance for a part of the projection, the distance to a nearest location in the image is determined, at which a part of the instrument is detectable in the image by using a predefined instrument detection algorithm, and c) determine the accuracy based on the determined distances; and
   wherein the accuracy determination unit is configured to subdivide the instrument as defined by the provided position and shape into regions and to determine the accuracy for each region of the instrument separately, in order to determine for different regions of the instrument as defined by the provided position and shape and of the image respective accuracies.

2. The visualization system as defined in claim 1, wherein the position, shape and image providing unit is configured to register the position and shape with the image for providing the alignment between the position and shape and the image.

3. An interventional system for performing an image-guided interventional procedure, the interventional system comprising:
   an interventional instrument to be used within a subject,
   an imaging device constructed to image the interventional instrument within the subject,
   a position and shape determination device constructed to determine a position and shape of the interventional instrument within the subject,
   a visualization system for visualizing an accuracy of an alignment of the position and shape of the interventional instrument with the image of the interventional instrument as defined in claim 1.

4. A visualization system for visualizing an accuracy of an alignment of a position and shape of an instrument, which has been determined by a position and shape determination device, with an image of the instrument, wherein the visualization system comprises:
   a position, shape and image providing unit configured to provide a) the position and shape and b) the image which are aligned to each other,
   an accuracy determination unit configured to determine the accuracy of the alignment based on the position and shape and based on the image, wherein the accuracy determination unit is configured to determine the accuracy for different regions of the instrument as defined by the position and shape and of the image and to determine a region, in which the determined accuracy indicates that it is insufficient, and
   a visualization unit configured to generate a visualization of the accuracy, wherein the visualization unit is configured to generate the visualization such that the determined region is indicated on at least one of a) a representation of the position and shape and b) the image;
   wherein the accuracy determination unit is configured to a) determine a projection of the instrument as defined by the provided position and shape onto the image under consideration of an image acquisition geometry which had been used for generating the provided image, b) determine distances for parts of the projection, wherein, for determining a distance for a part of the projection, the distance to a nearest location in the image is determined, at which a part of the instrument is detectable in the image by using a predefined instrument detection algorithm, and c) determine the accuracy based on the determined distances; and
   wherein the accuracy determination unit is configured to, for determining a distance for a part of the projection, determine the distance only within an area around the part, which has a predefined size.

5. The visualization system as defined in claim 4, wherein the accuracy determination unit is configured such that the predefined size depends on the size of the image.

6. The visualization system as defined in claim 5, wherein the accuracy determination unit is configured such that the predefined size increases with increasing size of the image.

7. The visualization system as defined in claim 1, wherein the accuracy determination unit is configured to determine distance features based on the determined distances and determine the accuracy based on the determined distance features.

8. The visualization system as defined in claim 7, wherein the accuracy determination unit is configured to use a trained classifier for determining the accuracy based on the distance features.

9. A visualization system for visualizing an accuracy of an alignment of a position and shape of an instrument, which has been determined by a position and shape determination device, with an image of the instrument, wherein the visualization system comprises:
- a position, shape and image providing unit configured to provide a) the position and shape and b) the image which are aligned to each other,
- an accuracy determination unit configured to determine the accuracy of the alignment based on the position and shape and based on the image, wherein the accuracy determination unit is configured to determine the accuracy for different regions of the instrument as defined by the position and shape and of the image and to determine a region, in which the determined accuracy indicates that it is insufficient, and
- a visualization unit configured to generate a visualization of the accuracy, wherein the visualization unit is configured to generate the visualization such that the determined region is indicated on at least one of a) a representation of the position and shape and b) the image;

wherein the accuracy determination unit is configured to a) determine a projection of the instrument as defined by the provided position and shape onto the image under consideration of an image acquisition geometry which had been used for generating the provided image, b) determine distances for parts of the projection, wherein, for determining a distance for a part of the projection, the distance to a nearest location in the image is determined, at which a part of the instrument is detectable in the image by using a predefined instrument detection algorithm, and c) determine the accuracy based on the determined distances; and wherein the accuracy determination unit is configured to determine distance features based on the determined distances and determine the accuracy based on the determined distance features; and wherein the accuracy determination unit is configured to determine the distance features such that they include at least one of a) an average of the determined distances and b) a fraction of the distances being larger than a predefined fraction threshold.

10. The visualization system as defined in claim 9, wherein the accuracy determination unit is configured to determine the distance features such that they include at least one of a) a maximum of i) an average of the determined distances and ii) an average of the determined further distances and b) a maximum of i) a fraction of the distances being larger than the predefined fraction threshold and ii) a fraction of the further distances being larger than the predefined fraction threshold.

11. The visualization system as defined in claim 1, wherein the position, shape and image providing unit is configured to provide a further image which shows the instrument and which is aligned with the position and shape, wherein the accuracy determination unit is configured to a) determine a further projection of the instrument as defined by the provided position and shape onto the further image under consideration of a further image acquisition geometry which had been used for generating the provided further image, b) determine further distances for parts of the further projection, wherein, for determining a further distance for a part of the further projection, the distance to a nearest location in the further image is determined, at which a part of the instrument is detectable in the further image by using the predefined instrument detection algorithm, and c) determine the accuracy also based on the determined further distances.

* * * * *